United States Patent
Sezginer et al.

(10) Patent No.: US 10,539,512 B2
(45) Date of Patent: Jan. 21, 2020

(54) BLOCK-TO-BLOCK RETICLE INSPECTION

(71) Applicant: KLA-Tencor Corporation, Milpitas, CA (US)

(72) Inventors: Abdurrahman Sezginer, Monte Sereno, CA (US); Patrick LoPresti, San Jose, CA (US); Joe Blecher, San Jose, CA (US); Rui-fang Shi, Cupertino, CA (US); Yalin Xiong, Pleasanton, CA (US); John Fielden, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/707,791

(22) Filed: Sep. 18, 2017

(65) Prior Publication Data

US 2018/0003647 A1    Jan. 4, 2018

Related U.S. Application Data

(63) Continuation of application No. 14/466,688, filed on Aug. 22, 2014, now Pat. No. 9,766,185.

(60) Provisional application No. 61/869,211, filed on Aug. 23, 2013.

(51) Int. Cl.
    *G06K 9/62*     (2006.01)
    *G01N 21/88*    (2006.01)
    *G01N 21/958*   (2006.01)
    *G06T 7/00*     (2017.01)

(52) U.S. Cl.
    CPC ..... *G01N 21/8851* (2013.01); *G01N 21/8806* (2013.01); *G01N 21/958* (2013.01); *G06T 7/001* (2013.01); *G01N 2021/8887* (2013.01); *G01N 2201/125* (2013.01); *G06T 2207/20224* (2013.01); *G06T 2207/30148* (2013.01)

(58) Field of Classification Search
    CPC ........... G06T 2207/30148; G01N 2021/95676; G03F 1/84
    See application file for complete search history.

(56) References Cited

U.S. PATENT DOCUMENTS

| 4,926,489 A | 5/1990 | Danielson et al. |
| 7,065,239 B2 | 6/2006 | Maayah et al. |

(Continued)

FOREIGN PATENT DOCUMENTS

| JP | 2006170809 A | 6/2006 |
| JP | 2010091425 A | 4/2010 |

(Continued)

OTHER PUBLICATIONS

JP Office Action dated Aug. 21, 2018 for Japanese Application No. 2016-536491.

*Primary Examiner* — Brian Werner
(74) *Attorney, Agent, or Firm* — Suiter Swantz pc llo

(57) ABSTRACT

Block-to-block reticle inspection includes acquiring a swath image of a portion of a reticle with a reticle inspection sub-system, identifying a first occurrence of a block in the swath image and at least a second occurrence of the block in the swath image substantially similar to the first occurrence of the block and determining at least one of a location, one or more geometrical characteristics of the block and a spatial offset between the first occurrence of the block and the at least a second occurrence of the block.

15 Claims, 10 Drawing Sheets

(56) References Cited

U.S. PATENT DOCUMENTS

| | | | |
|---|---|---|---|
| 7,526,119 B2 * | 4/2009 | Isomura | G06T 7/001 382/141 |
| 8,106,355 B1 | 1/2012 | Lauber et al. | |
| 8,155,428 B2 | 4/2012 | Lin et al. | |
| 2006/0133660 A1 | 6/2006 | Ogi et al. | |
| 2006/0280358 A1 | 12/2006 | Ishikawa | |
| 2007/0133860 A1 | 6/2007 | Lin et al. | |
| 2008/0166054 A1 * | 7/2008 | Tsuchiya | G06T 7/0004 382/194 |
| 2008/0304734 A1 | 12/2008 | Young et al. | |
| 2011/0176719 A1 | 7/2011 | Inoue et al. | |

FOREIGN PATENT DOCUMENTS

| | | |
|---|---|---|
| TW | 200921265 A | 5/2009 |
| WO | 2012148848 A2 | 11/2012 |

\* cited by examiner

BLOCK-TO-BLOCK RETICLE INSPECTION

CROSS-REFERENCE TO RELATED APPLICATION

The present application is related to and claims benefit of the earliest available effective filing date from the following applications. The present application constitutes a continuation patent application of U.S. patent application entitled BLOCK-TO-BLOCK RETICLE INSPECTION, naming Abdurrahman Sezginer, Patrick LoPresti, Joe Blecher, Rui-fang Shi, Yalin Xiong, and John Fielden as inventors, filed Aug. 22, 2014, application Ser. No. 14/466,688, which is a regular (non-provisional) patent application of U.S. Provisional Patent Application entitled BLOCK-TO-BLOCK RETICLE INSPECTION, naming Abdurrahman (Apo) Sezginer, Patrick LoPresti, Joe Blecher, Rui-fang Shi, Yalin Xiong, and John Fielden as inventors, filed Aug. 23, 2013, Application Ser. No. 61/869,211. U.S. patent application Ser. No. 14/466,688 and U.S. Provisional Patent Application No. 61/869,211 are incorporated herein by reference in their entirety.

TECHNICAL FIELD

The present invention generally relates to the inspection of lithographic reticles, and, more particularly, block-to-block inspection of lithographic reticles.

BACKGROUND

Reticle inspection has long been performed by die-to-die inspection, die-to-database inspection, and cell-to-cell inspection. Die-to-die inspection becomes impossible in settings where the reticle contains only a single die or the reticle contains dies of different designs. Die-to-database inspection is impractical in the integrated circuit (IC) due to the associated data flow infrastructure limitation of the IC fab and the large size of databases associated with reticle design. Cell-to-cell inspection is limited when comparing portions of the reticle, or mask, that are separated by large distances. Therefore, it is desirable to provide a method and system that cures the defects of the prior art.

SUMMARY

A method for block-to-block reticle inspection is disclosed. In one illustrative embodiment, the method includes acquiring a swath image of a portion of a reticle with a reticle inspection sub-system. In another illustrative embodiment, the method includes identifying a first occurrence of a block in the swath image and at least a second occurrence of the block in the swath image substantially similar to the first occurrence of the block. In another illustrative embodiment, the method includes determining at least one of a location, one or more geometrical characteristics of the block and a spatial offset between the first occurrence of the block and the at least a second occurrence of the block.

A method for design database assisted block-to-block reticle inspection is disclosed. In one illustrative embodiment, the method includes identifying a set of repeating blocks of a reticle within a design database for the reticle. In one illustrative embodiment, the method includes determining one or more spatial characteristics associated with the set of repeating blocks of the reticle. In one illustrative embodiment, the method includes storing the one or more spatial characteristics associated with the set of repeating blocks of the reticle. In one illustrative embodiment, the method includes acquiring an image of a portion of the reticle with a reticle inspection sub-system. In one illustrative embodiment, the method includes identifying a first portion of the acquired image corresponding with a first member of the set of repeating blocks according to the stored spatial characteristics associated with the set of repeating blocks. In one illustrative embodiment, the method includes identifying a second portion of the acquired image that corresponds to a second member of the set of repeating blocks according to the stored spatial characteristics associated with the set of repeating blocks. In one illustrative embodiment, the method includes aligning the first portion of the acquired image and the second portion of the acquired image. In one illustrative embodiment, the method includes generating a difference of image by performing a subtraction routine on the first portion of the acquired image and the second portion of the acquired image. In one illustrative embodiment, the method includes identifying one or more defects on the reticle with the generated difference image.

A system for block-to-block reticle inspection is disclosed. In one illustrative embodiment, the system includes a reticle inspection sub-system configured for scanning a swath image of a portion of a reticle with a reticle inspection system. In one illustrative embodiment, the system includes a controller including one or more processors configured to execute a set of program instructions maintained on a memory, the program instructions configured to: identify a first occurrence of a block in the swath image and at least a second occurrence of the block in the swath image substantially similar to the first occurrence of the block; and determine at least one of a location, one or more geometrical characteristics of the block and a spatial offset between the first occurrence of the block and the at least a second occurrence of the block.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Figure 1A:
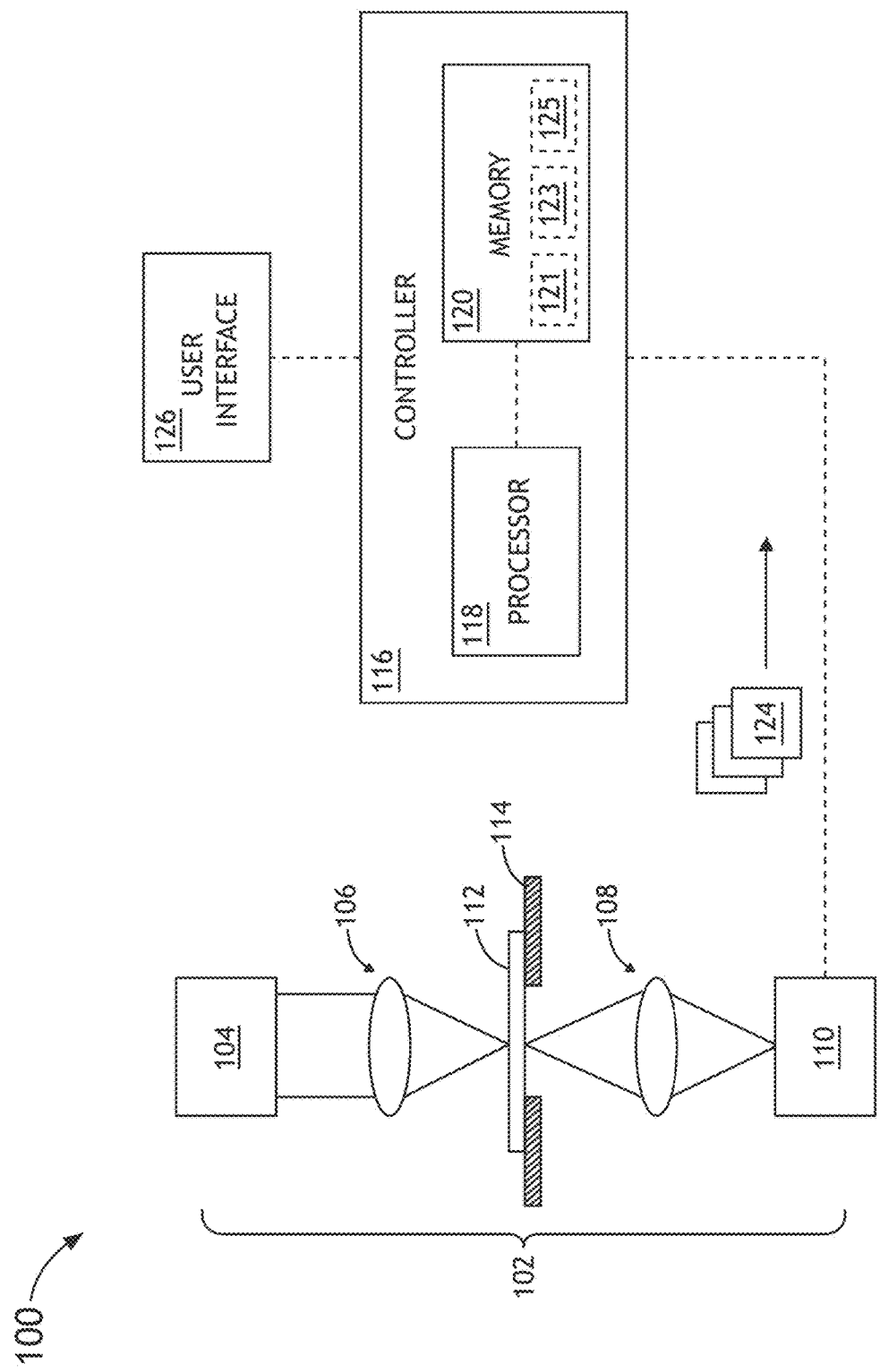
FIG. 1A illustrates a block diagram view of block-to-block reticle inspection system, in accordance with one or more embodiments of the present disclosure.

Reference will now be made in detail to the subject matter disclosed, which is illustrated in the accompanying drawings.

Referring generally to FIGS. 1A-2C, systems and methods for block-to-block reticle inspection are described in accordance with the present disclosure. Embodiments of the present disclosure are directed to performing block-to-block reticle inspection with and without design database assistance. Some embodiments of the present disclosure serve to carry inspection of a reticle having a single die, when in the absence of a design database for the reticle pattern. In addition, some embodiments of the present disclosure identify a block of patterns occurring multiple times in a die and then compare images of the repeating blocks to each other in order to detect defects. Additional embodiments of the present disclosure serve to perform block-to-block reticle inspection with the assistance of a design database.

Integrated circuits frequently contain repeating blocks. In this regard, a single integrated circuit may include two or more repeating blocks. For example, cores of a multi-core CPUs may be identical at some front-end layers of the given chip. In this example, each core may have multiple identical instances of registers and arithmetic logic units (ALUs). In addition, a GPU may include an array of ALUs. Further, a field programmable gate array may include an array of identical units. Similarly, an ASIC may exhibit repeated instances of an IP block, such as an FFT engine. Further, a memory chip may include identical blocks of memory cores separated by identical blocks of support circuitry, such as read-write amplifiers, buffers and the like.

Repeating blocks within a die of a given integrated circuit may display significant spatial separation, a feature the significantly differentiates block-to-block inspection from cell-to-cell inspection. For example, two or more repeating blocks within a single die may be separated by a distance on the order of approximately 100 μm to 10 mm. In one embodiment, the reticle inspection process of the present disclosure may be carried out via parallel processing, where each processor has access to a patch of the reticle image. It is noted herein that in the case of cell-to-cell inspection a given processor can only compare cells that are in the same patch, where a patch can be 1024×2048 pixels in size and the pitch of pixels can be 55 to 125 nanometers in the reticle plane. As such, cell-to-cell inspection is not effective if the cells are farther apart than approximately 2048×125 nm=256 μm. Integrated circuits can have repeating blocks that are millimeters apart.

Further, die-to-die based inspection is rendered useless in settings where a reticle includes a single die or includes dies of different designs.

The remainder of the present disclosure describes embodiments suitable for identifying blocks within a single die of a reticle via reticle inspection with and without design database assistance.

For the purposes of the present disclosure, OPC (optical proximity compensation) includes moving edge-segments of main features, inserting sub-resolution assist features, inverse lithography technology (ILT), and source-mask optimization (SMO). A pre-OPC design database is highly hierarchical and contains many repeating cells even in the case of a random-logic chip. In one embodiment, "hierarchy" in a design database describes sets of polygons comprising other sets of polygons. For example, the database may indicate that set-A is the union of sets-a, b, c, . . . ; and set-a is the union of sets-α, β, . . . ; and instances (copies) of set-A are located at $(x_1,y_1)$, $(x_2,y_2)$, . . . and so on. Repeating blocks can be discovered from the hierarchy of a design database without searching for repeating blocks over a list of individual polygons or a pixelated image. Cells that are identical in the pre-OPC database are altered following OPC if they have different environments. Still, a central portion of such cells may repeat identically in the post-OPC database. Keeping repeating cells identical in the post-OPC database saves computation time and reduces OPC-induced variability in critical dimension and overlay measurements. As such, a post-OPC database typically has non-zero hierarchy. Even if the post-OPC database is not hierarchical, if the OPC process is reproducible, some core portion of repeating cells that are distant from non-repeating environments may converge to the same solution.

FIG. 1A illustrates a block diagram view of block-to-block reticle inspection system 100, in accordance with one or more embodiments of the present disclosure. In one embodiment, the system 100 includes a reticle inspection sub-system 102. In one embodiment, the reticle inspection sub-system 102 is configured to perform an inspection process on a reticle 112 secured on a reticle stage 114. In one embodiment, as shown in greater detail further herein, the reticle inspection sub-system 102 may acquire a swath image 124 of a portion of a reticle 112. The defining characteristic of a swath is that entire swath image 124 is held in a memory, and is available for processing, at the same time. In an implementation, a swath is the region that is imaged as the reticle stage 114 moves linearly in one direction, from one edge of the inspection area to its opposite edge.

In one embodiment, the reticle inspection sub-system 102 includes one or more illumination sources 104. The illumination source 104 may include any illumination source known in the art of reticle inspection. For example, the illumination source 104 may include, but is not limited to, a narrowband source (e.g., one or more lasers) or a broadband source (e.g., broadband lamp with or without filtering).

In one embodiment, the reticle inspection sub-system 102 includes a set of illumination optics 106. The illumination optics 106 may include any one or more optical elements suitable for receiving illumination from the illumination source 104 and illuminate the reticle 112. For example, the one or more illumination optics 106 may include, but are not limited to, one or more lenses, mirrors, beam splitters, collimators, filters, polarizing elements and the like. For instance, the illumination optics 106 may include a lens for focusing light from the illumination source 104 onto the plane of the reticle 112.

In another embodiment, the reticle inspection sub-system 102 includes a set of collection, or imaging, optics 108. The collection, imaging, optics 108 may include any one or more optical elements suitable for collecting illumination from the reticle 112 (via transmission, scattering, reflection, diffraction and the like) and directing and/or imaging the reticle 112 onto the detector 110. For example, the one or more illumination optics 108 may include, but are not limited to, one or more lenses, mirrors, beam splitters, collimators, filters, polarizing elements and the like. For instance, the illumination optics 108 may include a magnification lens.

The detector 110 may include any detector known in the art of reticle inspection. For example, the detector 110 may include, but is not limited, one or more CCD devices, one or more TDI devices, one or more PMT devices and the like.

It is noted herein that the reticle inspection sub-system 102 may be configured to operate with any spectral range of illumination known in the art of reticle inspection. For example, the reticle inspection sub-system 102 may include, but is not limited to, a visible inspection sub-system, an ultraviolet inspection sub-system, a deep ultraviolet inspection sub-system, an extreme ultraviolet inspection sub-system or a vacuum ultraviolet inspection sub-system. In other embodiment, the reticle inspection sub-system 102 may include a charged particle based reticle inspection sub-system 102. For example, the reticle inspection sub-system 102 may include an electron beam based reticle inspection sub-system 102.

Reticle inspection and the scanning of image swaths is described generally in U.S. patent application Ser. No. 14/223,709 to Bing Li et al., filed on Mar. 24, 2014, which is incorporated herein by reference in the entirety. Reticle inspection is also generally described in U.S. Pat. No. 7,133,548 to Kenan et al., issued on Nov. 7, 2006, which is incorporated herein by reference in the entirety.

In another embodiment, the system 100 includes a controller 116. In one embodiment, the controller 116 includes one or more processors 118 and one or more memories 120 (e.g., non-transitory memory). In one embodiment, the controller 116 is communicatively coupled to detector 110 of the reticle inspection sub-system 102. In this regard, upon acquiring image 124, the detector 110 may transmit the swath image 124 to the controller 116. In another embodiment, the one or more processors 118 may execute a block-to-block inspection module 121 maintained in memory 120. The block-to-block inspection module 121 may include a set of program instructions configured to cause the one or more processors 118 to execute any of the steps described throughout the present disclosure. For example, the block-to-block inspection module 121 may cause the one or more processors 118 to: acquire a swath image 124 of a portion of a reticle 112 with a reticle inspection sub-system 102; identify a first occurrence of a block in the swath image and at least a second occurrence of the block in the swath image 124 substantially similar to the first occurrence of the block; and determine at least one of a location, one or more geometrical characteristics of the block and a spatial offset between the first occurrence of the block and the at least a second occurrence of the block.

The one or more processors 118 of controller 116 may include any one or more processing elements known in the art. The one or more processors 118 may include any microprocessor-type device configured to execute software algorithms and/or instructions. In one embodiment, the one or more processors 118 may include of a desktop computer, mainframe computer system, workstation, image computer, parallel processor, or other computer system (e.g., networked computer) configured to execute a program configured to operate the system 100, as described throughout the present disclosure. It should be recognized that the steps described throughout the present disclosure may be carried out by a single computer system or, alternatively, multiple computer systems. In general, the term "processor" may be broadly defined to encompass any device having one or more processing elements, which execute program instructions (e.g., module 121 or module 127) from a non-transitory memory medium 120. Moreover, different subsystems of the system 100 (e.g., display, user interface, reticle inspection sub-system 102) may include a processor or logic elements suitable for carrying out at least a portion of the steps described throughout the present disclosure. Therefore, the above description should not be interpreted as a limitation on the present invention but merely an illustration.

The memory 120 may include any storage medium known in the art suitable for storing program instructions executable by the associated one or more processors 118. For example, the memory 120 may include, but is not limited to, a read-only memory, a random access memory, a magnetic or optical memory device (e.g., disk), a magnetic tape, a solid state drive and the like. In another embodiment, it is noted herein that the memory 120 is configured to store one or more results from the reticle inspection sub-system 102 (e.g., image database 123) and/or the output of the various steps described herein (e.g., block information database 125). It is further noted that memory 120 may be housed in a common controller housing with the one or more processors 118. In another embodiment, the memory 120 may be located remotely with respect to the physical location of the processors 118 and controller 116. For instance, the one or more processors 118 of controller 116 may access a remote memory (e.g., server), accessible through a network (e.g., internet, intranet and the like) to acquire the swath images 124.

In another embodiment, the system 100 includes a user interface 126. The user interface 126 may include any user interface known in the art. For example, the user interface 126 may include a user input device and/or a display for displaying data to a user and receiving user input instructions. For example, the user input device may include, but is not limited to, a keyboard, a keypad, a touchscreen, a lever, a knob, a scroll wheel, a track ball, a switch, a dial, a sliding bar, a scroll bar, a slide, a handle, a touch pad, a paddle, a steering wheel, a joystick, a bezel input device or the like. The display device may include any display device known in the art. In one embodiment, the display device may include, but is not limited to, a liquid crystal display (LCD). In another embodiment, the display device may include, but is not limited to, an organic light-emitting diode (OLED) based display. In another embodiment, the display device may include, but is not limited to a CRT display. In a general sense, any display device capable of integration with a user interface device (e.g., touchscreen, bezel mounted interface, keyboard, mouse, trackpad, and the like) is suitable for implementation in the present invention. In the case of a touchscreen interface device, those skilled in the art should recognize that a large number of touchscreen interface devices may be suitable for implementation in the present invention. For instance, the display device may be integrated with a touchscreen interface, such as, but not limited to, a capacitive touchscreen, a resistive touchscreen, a surface acoustic based touchscreen, an infrared based touchscreen, or the like. In a general sense, any touchscreen interface capable of integration with the display portion of the display device is suitable for implementation in the present invention.

Figure 1B:
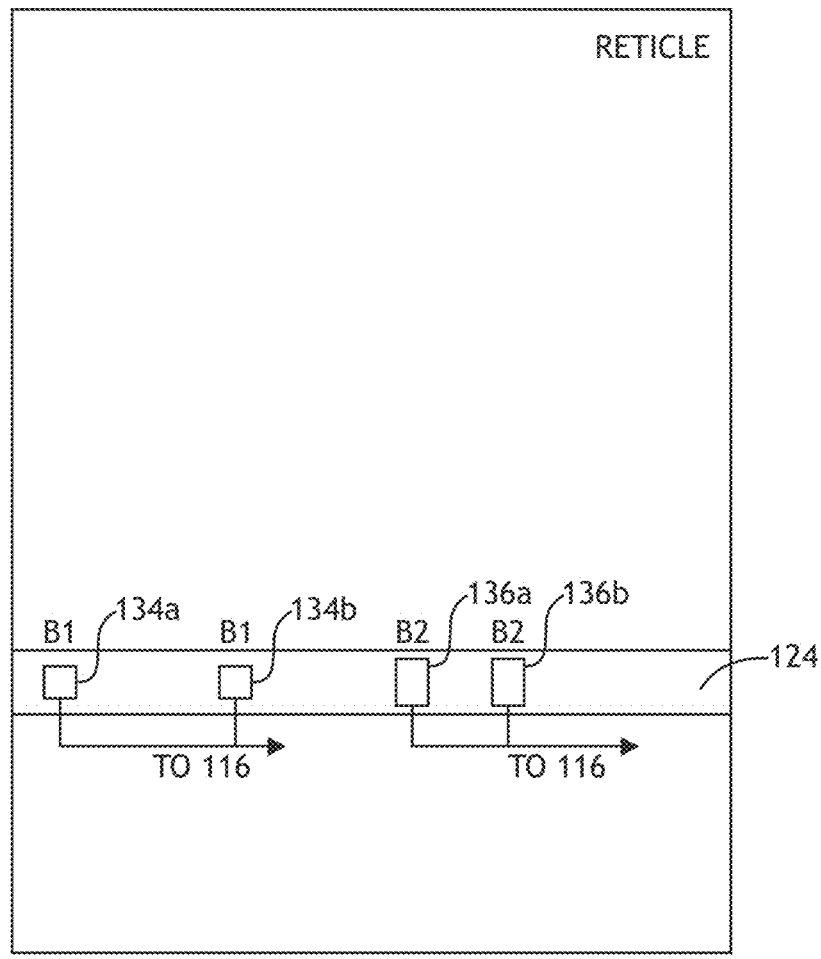
FIG. 1B illustrates a conceptual view of a swath image acquired with a reticle inspection sub-system from a reticle, in accordance with one embodiment of the present disclosure.

FIG. 1B illustrates a conceptual view of a swath image 124 acquired with the reticle inspection sub-system 102 from the reticle 112, in accordance with one embodiment of the present disclosure. As shown in FIG. 1B, one or more swath images 124 may be acquired from a portion of the reticle 112. In one embodiment, a given swath image 124 may include a first occurrence 134a of block B1 and at least a second occurrence 134b of the block B1. In addition, the given swath image 124 may include a first occurrence 136a of block B2 and at least a second occurrence 136b of the block B2. It is recognized herein that only a single swath 124 image is depicted in the reticle image 112. This depiction is not intended as a limitation on the present invention and is provided for clarity and illustrative purposes only.

The embodiments of the system 100 illustrated in FIGS. 1A and 1B may be further configured as described herein. In addition, the system 100 may be configured to perform any other step(s) of any of the method embodiment(s) described herein. The following method embodiments relate to block-to-block reticle inspection. It is generally recognized that system 100 is suitable for implementing the inspection level and data processing level steps of the following embodiments. It is noted, however, the methods described below are not limited to the architecture of system 100.

Figure 1C:
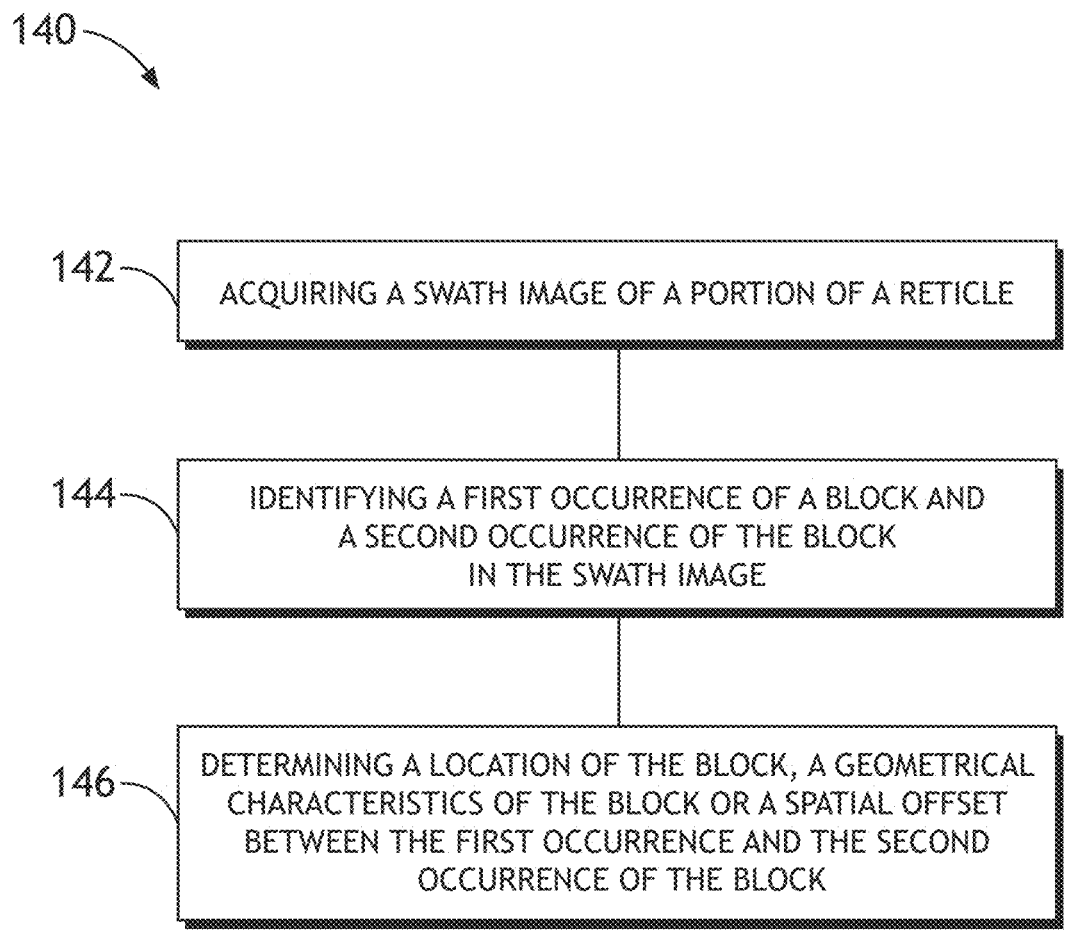
FIG. 1C illustrates a flow diagram depicting a method for block-to-block reticle inspection system, in accordance with one or more embodiments of the present disclosure.

FIG. 1C illustrates a flow diagram depicting a process 140 for block-to-block reticle inspection, in accordance with one or more embodiments of the present disclosure.

In step 142, a swath image of a portion of a reticle 112 with a reticle inspection sub-system 102 is acquired. For example, as shown in FIGS. 1A-1B, the reticle inspection sub-system 102 may acquire an image of the reticle 112 containing one or more swaths. In one embodiment, the reticle inspection sub-system 102 scans a swath image 124 of the reticle 112 during an inspection process of the reticle 112. It is noted herein that a "swath" is interpreted as one pass of the overall scan across the reticle 112. For example, multiple swaths may be acquired via a serpentine or raster scanning process. In another embodiment, the acquired swath image 124 is stored in memory 120. For example, the swath image 124 and the associated swaths 132 may be stored in an image data base 123 for later use. It is further noted herein that the swath image 124 may be as wide (horizontal direction in FIG. 1B) as the die in the scan dimension. In the orthogonal dimension, the swath image 124 may be of limited size. For instance, the non-scanning dimension may have a size in the range of, but not limited to, 128 to 2048 pixels. It is noted herein that the size of the swath image 124 may depend the sizes of the detector array, buffers, data busses, and memory that are available for the particular reticle inspection sub-system 102.

In one embodiment, a user may provide coordinates of a die of the reticle 112 to be inspected with respect to a reference point on the reticle 112. For example, a user may provide die coordinates for inspection to the controller 116 via user interface 126. Then, the reticle inspection sub-system 102 may then scan the die and store the corresponding swath image 124 in memory 120 in the image database 123.

It is further noted that the one or more processors 118 have access to the entire swath image 124 stored in the database 123 of memory 120. For example, in the event each pixel for a given image has an 8-bit value, a pixel pitch of 72 nm, the swath image is 256 pixels high and the die is 10 cm wide on the reticle 112, then storing the swath image 124 may require 339 MB of memory. It is noted herein that the above example is provided merely for illustrative purposes and is intended as a limitation on the present invention.

In step 144, a first occurrence of a block in the swatch image 124 and at least a second occurrence of the block in the swath image 124 substantially similar to the first occurrence of the block are identified. For example, as shown in FIGS. 1A-1B, the controller 116 may identify a first occurrence 134a of block B1 in the swatch image 124 and a second occurrence 134b of the block B1 in the swath image 124. By way of another example, the controller 116 may identify a first occurrence 136a of block B2 in the swatch image 124 and a second occurrence 136b of the block B2 in the swath image 124.

In one embodiment, process 140 may find blocks repeating along a given swatch direction (e.g., horizontal direction in FIG. 1B). It is noted herein that if a block repeats in two dimensions then it must repeat in each row going through the die. In one embodiment, the process 140 may check for repeating blocks in a first direction. Then, in the event there are repeating blocks in the first direction, the process 140 may check the reticle image to see if the block repeats in the second direction (orthogonal to the first direction).

In one embodiment, the step of identifying a first and second occurrence of blocks includes a sub-step of adding or averaging each column of the swatch image 124. In this regard, the swath image 124 may be reduced to a row vector represented as:

$$[r_1, r_2, \ldots, r_N] \quad (1)$$

In one embodiment, the mean of the row vector may be subtracted from the row vector such that the resulting row vector has a zero mean. The result row vector is given by:

$$r(j) = \frac{1}{M}\sum_{i=1}^{M} I(i,j) - \frac{1}{MN}\sum_{j'=1}^{N}\sum_{i'=1}^{M} I(i',j') \quad (2)$$

The number I(i,j) represents the image intensity at pixel (i,j) and M and N are the number of rows and columns in the swath image 124, respectively. In another embodiment, one row of the swath image 124 may be selected instead of averaging rows.

In another embodiment, the step 144 of identifying a first and second occurrence of blocks includes a sub-step of generating an autocorrelation array of the swath image 124. In one embodiment, the autocorrelation of the above row vector is analyzed by itself.

In one embodiment, the autocorrelation of the entire above row vector is analyzed by itself. This relationship is represented by:

$$c_n = \sum_{j=1}^{N-n} r(n+j)r(j) \quad (3)$$

The index n denotes the shift between two copies of the row vector and the integer N is the number of pixels in the scan direction. It is recognized herein that this approach is relatively fast. However, this correlation approach indicates repeating blocks only if the block area is a non-negligible fraction of the swath area.

In another embodiment, auto correlation of a portion of the row vector is analyzed with the entire row vector. This relationship is represented by:

$$c_{n,m,w} = \sum_{j=m}^{min(m+w-1,N-n)} r(n+j)r(j) \quad (4)$$

The portion of the row vector (or the "window") is w pixels wide and starts at pixel m. Further, the autocorrelation depends on the shift n and window parameters w and m. The window width w is fixed and pre-determined. It is noted herein that this operation may be repeated for multiple values of m that are incremented by w. For each value of m the following steps are repeated. The autocorrelation peaks that result from the existence of repeating blocks may not display a good signal-to-noise ratio in the first autocorrelation approach (3). It is recognized herein that the signal-to-noise may be improved using the second correlation approach (4) with a window width that is less than the swath width. It is further noted that the second approach (4) is less restrictive, but generally more computationally-intensive than approach (3).

In another embodiment, the step 144 of identifying a first and second occurrence of blocks includes a sub-step of identifying a location of one or more local peaks in the autocorrelation array. For example, as shown in FIG. 1A, the controller 116 may identify a location of one or more local peaks in the autocorrelation array from the previous sub-step. In this regard, the controller 116 may find local peaks in the autocorrelation array, denoted as $c_n$. For example, a local peak may occur at index n* where:

$$c_{n^*} > (1+\delta)c_{n^*+k} \text{ for all } k \qquad (5)$$

Where k is in some interval represented by:

$$k \in [-K,K] \qquad (6)$$

Where the interval has a pre-selected length. In one embodiment, the value of the parameter δ is 0.1. It is further noted that the location of a peak n* may indicate the distance in pixels between two identical blocks.

Figure 1D:
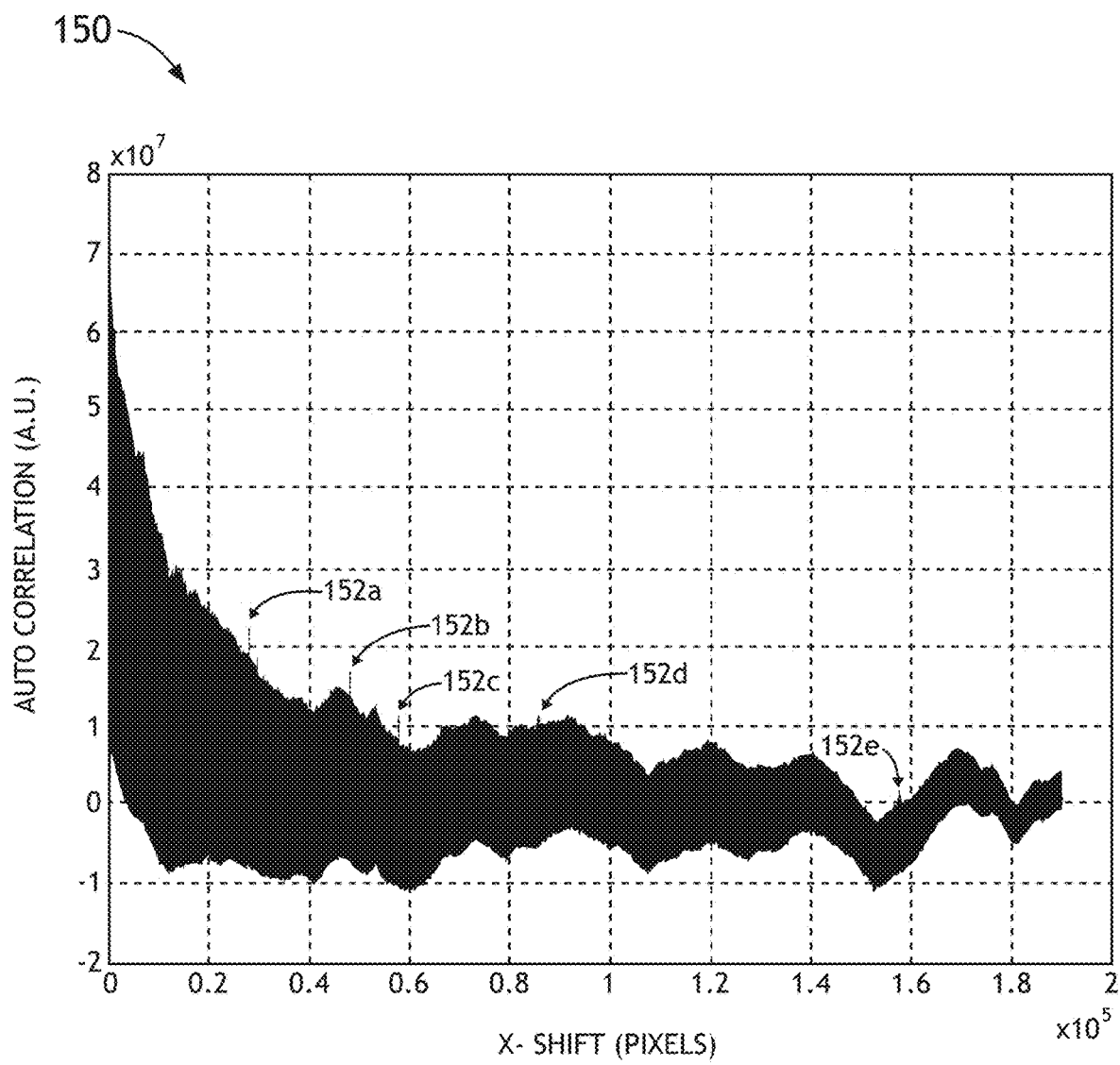
FIG. 1D illustrates autocorrelation as a function of shift along a first direction measured in pixels, in accordance with one or more embodiments of the present disclosure.

FIG. 1D illustrates the autocorrelation (in arbitrary units) as a function of shift along a first direction (x-direction) measured in pixels. In this example, the row vector is the column-average of a 128-pixel height swath image 124. It is noted herein that the sharp peaks (152a-152e) may occur at shift values that equal the offset between two repeating blocks. It is further noted herein that the autocorrelation function oscillates rapidly due to smaller periods of periodic or quasi-periodic patterns.

Referring again to FIG. 1C, in another embodiment, the step 144 of identifying a first and second occurrence of blocks includes a sub-step of generating a shifted swath image by translating, or shifting, the swath image 124 according to the identified location of the one or more local peaks. Further, the step 114 includes a sub-step of generating a difference image by performing a subtraction routine on the shifted swatch image from the swath image 124.

In one embodiment, as shown in FIG. 1A, the controller 116 may generate a shifted swath image by translating, or shifting, the swath image 1124 according to the identified location of the one or more local peaks identified above. In another embodiment, the controller 116 may generate a difference image by performing a subtraction routine (e.g., subtraction, weight subtraction and the like) on the shifted swatch image from the swath image 124.

In one embodiment, the controller 116 may shift the row vector (described above) by n* and evaluate the difference between the row vector and its shifted version. This operation is represented by:

$$d(j) = r(j) - r(n^*+j) \qquad (7)$$

In another embodiment, the controller 116 may analyze the interval given by:

$$[j_0, j_1] \text{ where } |d(j)| < \varepsilon; j_0 \le j \le j_1 \qquad (8)$$

It is noted herein that the tolerance ε may be selected such that the difference in the images of repeating patterns is less than ε. The tolerance allows for tolerable amounts of focus vibration, plate noise, instrument noise, alignment error, reticle tilt and the like.

Figure 1E:
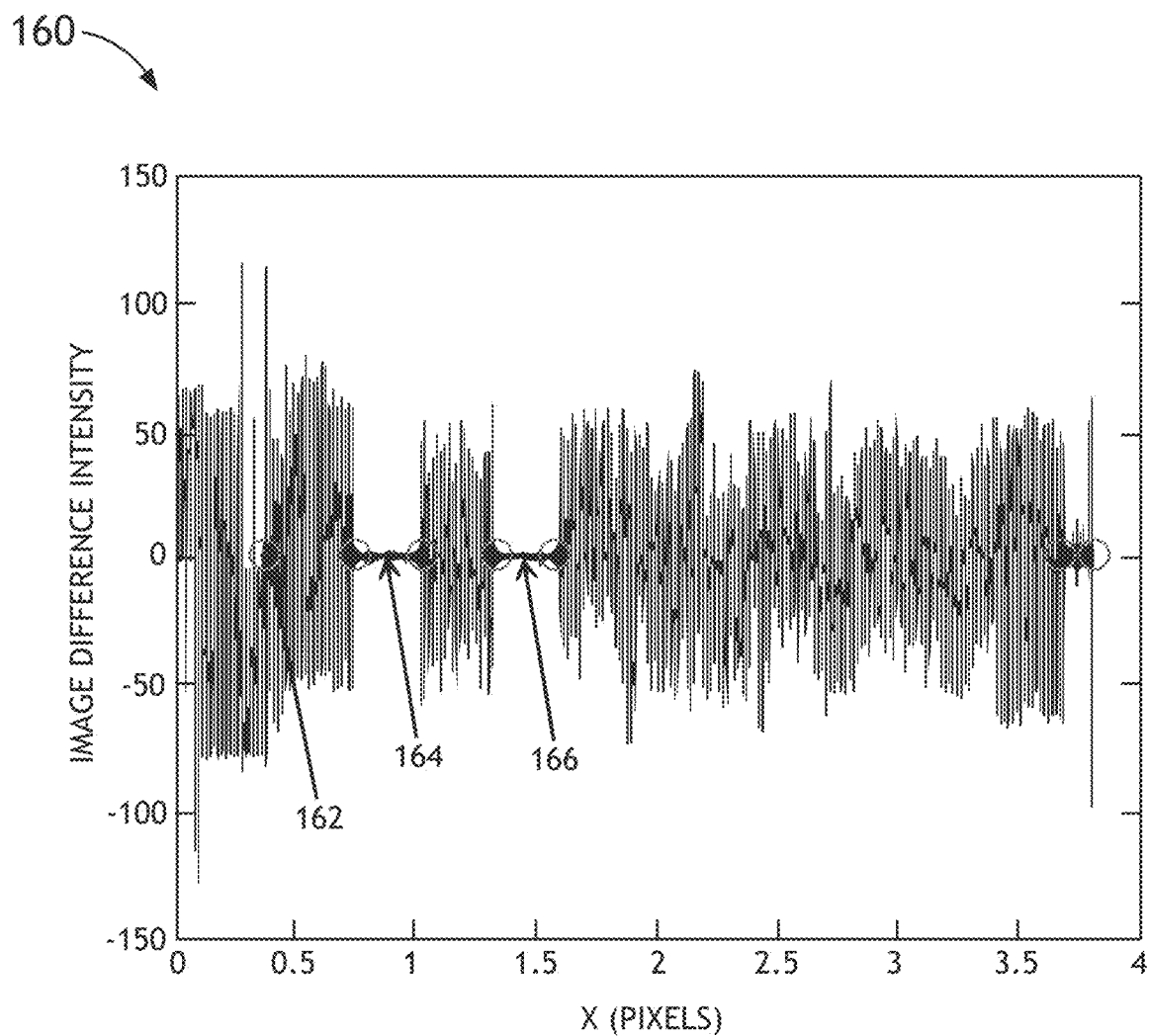
FIG. 1E illustrates a swath row vector shifted according to the left-most peak illustrated in FIG. 1D and subtracted from the un-shifted row vector, in accordance with one or more embodiments of the present disclosure.

FIG. 1E illustrates the swath row vector shifted according to the left-most peak illustrated in FIG. 1D and subtracted from the un-shifted row vector. As shown in FIG. 1E, the image intensity at the repeating blocks nearly cancel. In this regard, the controller 116 (or a user) may identify the bounds of possible repeating blocks along a given axis (e.g., x-axis). In FIG. 1E, labels 162, 164 and 166 identify candidate repeating blocks.

In another embodiment, prior to generating a difference image, the shifted swath image is aligned with the swath image at a sub-pixel resolution. In this regard, images that are subtracted from one another may be aligned with sub-pixel resolution prior to subtraction. In one embodiment, the following routing may be applied to carried out this alignment:

$$Q = [I_{0,0} I_{0,1} I_{0,-1}]$$

$$I_{0,0}$$

$$I_{m,n}(i,j) = I_{0,0}(i+m, j+n)$$

$$c = Q^{\#} I_{0,n^*} = (Q^T Q)^{-1} Q^T I_{0,n^*}$$

$$\text{diff} = I_{0,n^*} - Qc \qquad (9)$$

Where $I_{0,0}$ is a column vector formed from a 2D or 1D an image. It is recognized herein that the above routine may find a linear combination of un-shifted, left-shifted, and right-shifted images of a first block that best fits a second block that is n* pixels away from the first block. It is further noted herein that all columns of Q and the right-hand-side $I_{0,n^*}$ have the same number of valid pixels. It is further noted that if needed additional shifts (e.g., more than three columns) may be included in matrix. It is recognized herein indicates three image bases of un-shifted, left-shifted by one pixel and right-shifted by one pixel are often sufficient for good sub-pixel alignment. In another embodiment, an alignment method may employ one or more sinc interpolation filters or apply a linearly progressing phase shift in the Fourier transform domain.

Figure 1F:
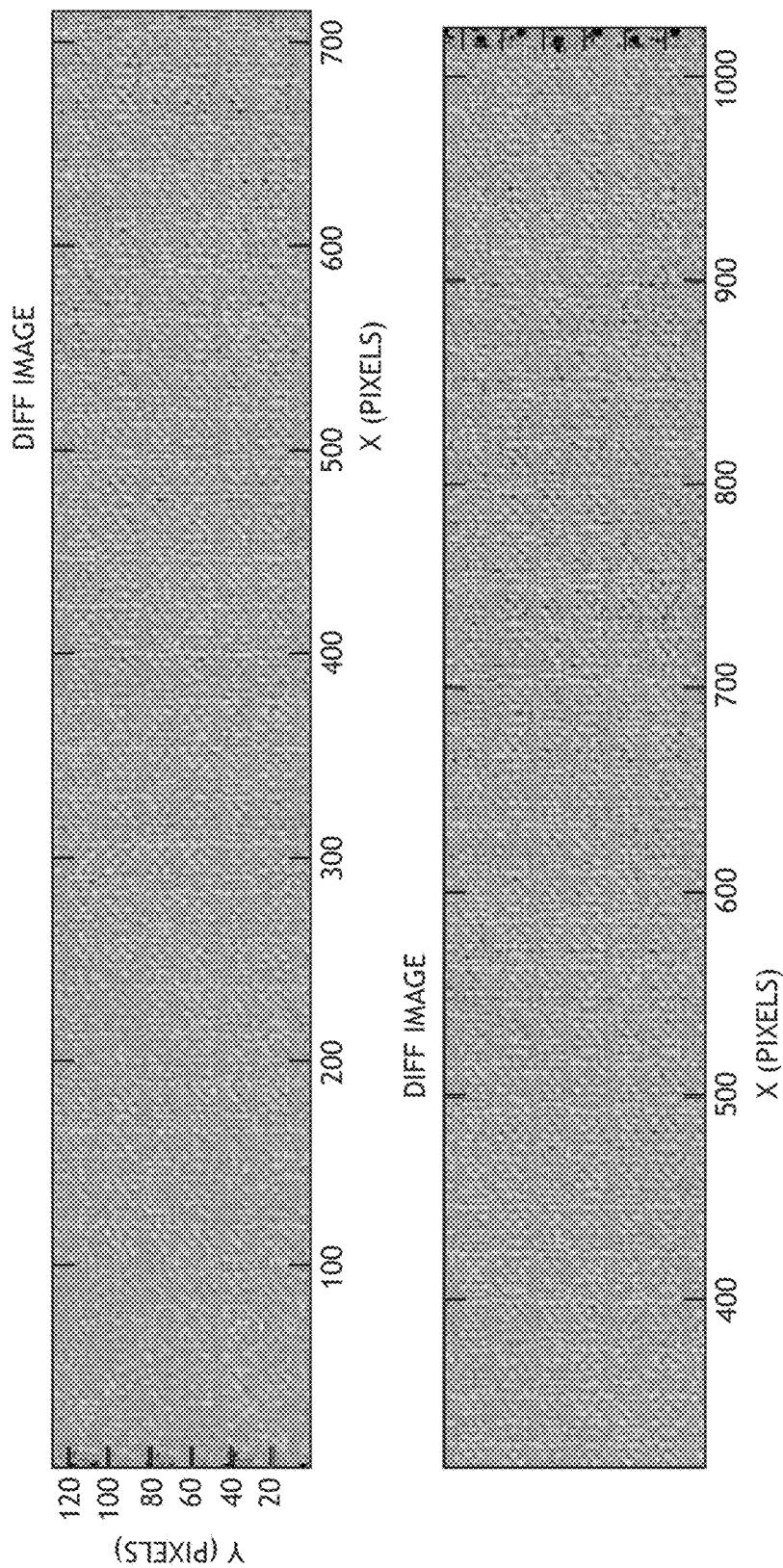
FIG. 1F illustrates a two-dimensional difference image corresponding with the repeating blocks in FIG. 1E, in accordance with one or more embodiments of the present disclosure.

FIG. 1F illustrates a two-dimensional difference image 170 corresponding with the repeating block 162 in FIG. 1E, in accordance with one or more embodiments of the present disclosure.

Referring again to FIG. 1C, in another embodiment, the step 144 of identifying a first and second occurrence of blocks includes a sub-step of identifying one or more regions in the difference image having a parameter value below a selected tolerance level. In one embodiment, the controller 116 may evaluate the two-dimensional image difference generated in the previous sub-step. In this regard, the controller 116 may evaluate the image difference:

$$D(i,j) \text{ for } j_0 \le j \le j_1 \qquad (10)$$

For example, the image difference may be represented by:

$$D(i,j) = I(i,j) - I(i, j+n^*); j_0 \le j \le j_1 \qquad (11)$$

Where the controller 116 may search for an interval $[i_0, i_1]$ of rows in which the difference is small:

$$|D(i,j)| < \varepsilon; i_0 \le i \le i_1, j_0 \le j \le j_1 \qquad (12)$$

In the event this condition is satisfied, the box $[i_0,i_1] \times [j_0, j_1]$ contains a repeating block. It is further noted that a copy of this block is located at $[i_0,i_1] \times [j_0+n^*, j_1+n^*]$.

Figure 1G:
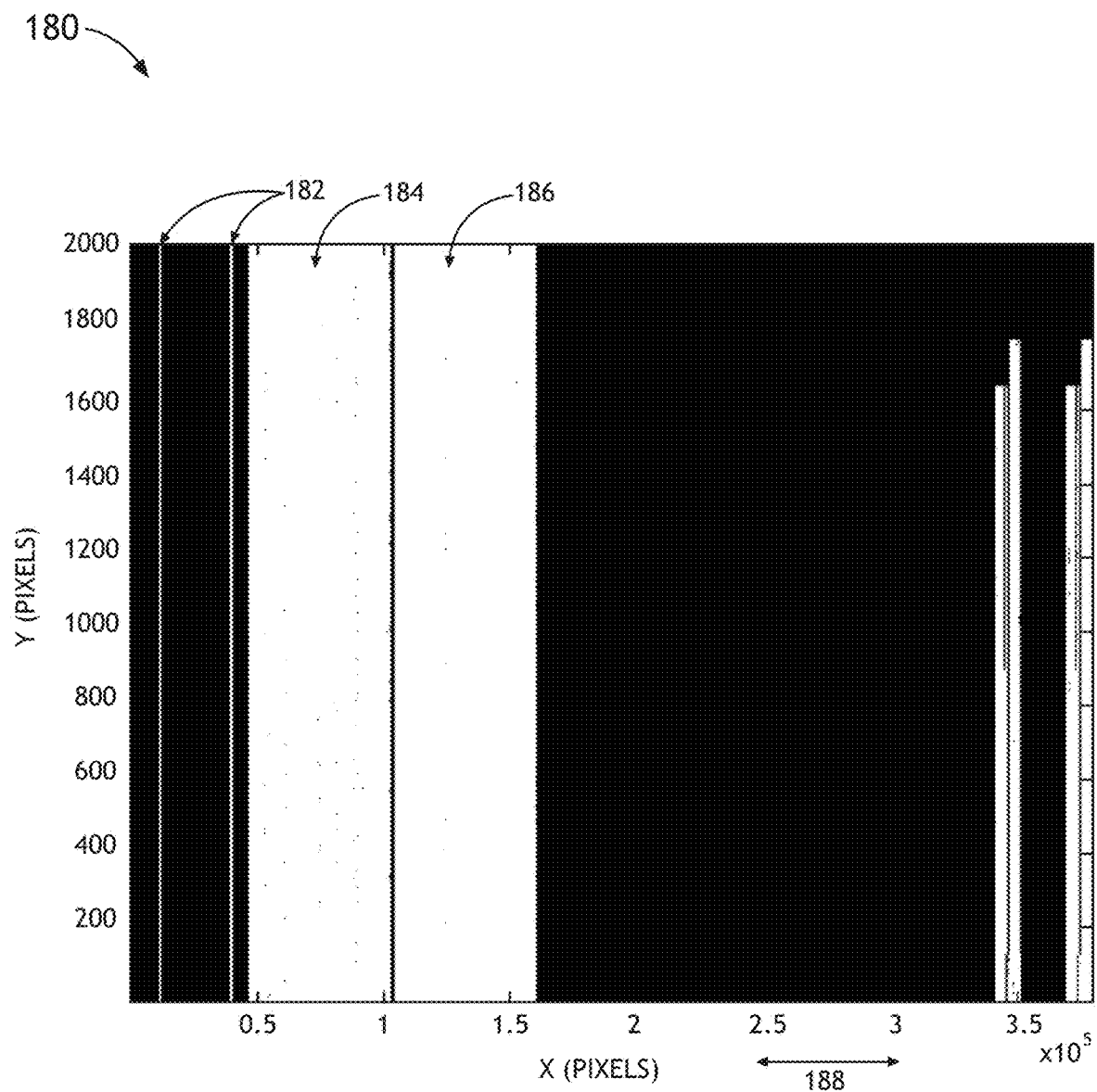
FIG. 1G illustrates a pixel swath containing multiple repeating blocks, in accordance with one or more embodiments of the present disclosure.

FIG. 1G is a gray-scale map of $|D(i,j)|$ for a pixel swath containing repeating blocks. Dark shades indicate high values and light shades indicate small values. For example, the pixel swatch may have, but is not limited to, a size of 380228×2048 pixels. As shown in FIG. 1G, the white areas represent repeating blocks. The reference numbers 182, 184 and 186 of FIG. 1G correspond to the features 162, 164 and 166, respectively, in FIG. 1E. By way of non-limiting example, the double arrow 188 may 50,000 pixels or 3.6 mm along the x-axis.

Referring again to FIG. 1C, in step 146, at least one of a location, one or more geometrical characteristics of the block and a spatial offset between the first occurrence of the block and the at least a second occurrence of the block is determined. For example, the controller 116 may extract the location, one or more geometrical characteristics of the block (e.g., shape) and a spatial offset (i.e., shift) between the first occurrence of the block and the at least a second occurrence of the block. For instance, based on the analysis above one or more spatial characteristics, including, but not limited to, the location, one or more geometrical characteristics of the block (e.g., shape) and a spatial offset (i.e., shift) between the first occurrence of the block and the at least a second occurrence of the block may be found once the repeating blocks are identified. In another embodiment, the controller 116 stores at least one of a location, one or more geometrical characteristics of the block and a spatial offset between the first occurrence of the block and the at least a second occurrence of the block in a spatial characteristics database 125 in memory 120. It is noted herein that the spatial characteristics found and stored by the controller 116 associated with one or more blocks are not limited to those provided above, which are provided merely for illustrative purposes.

In another embodiment, the controller 116 may record the bounding boxes of repeating blocks. It is noted that the repeating blocks may not necessarily have a rectangular or a simply-connected domain.

In one embodiment, the one or more geometrical characteristics are stored in memory 120 by storing a logical-valued array, wherein the logical-value is indicative one or more pixels in a repeating block In an embodiment we save the logical-valued array.

In one embodiment, the following logical-valued array is stored:

$$L(i,j) = \{|D(i,j)| < \varepsilon\}; \ i_0 \le i \le i_1, \ j_0 \le j \le j_1 \tag{13}$$

Figure 2A:
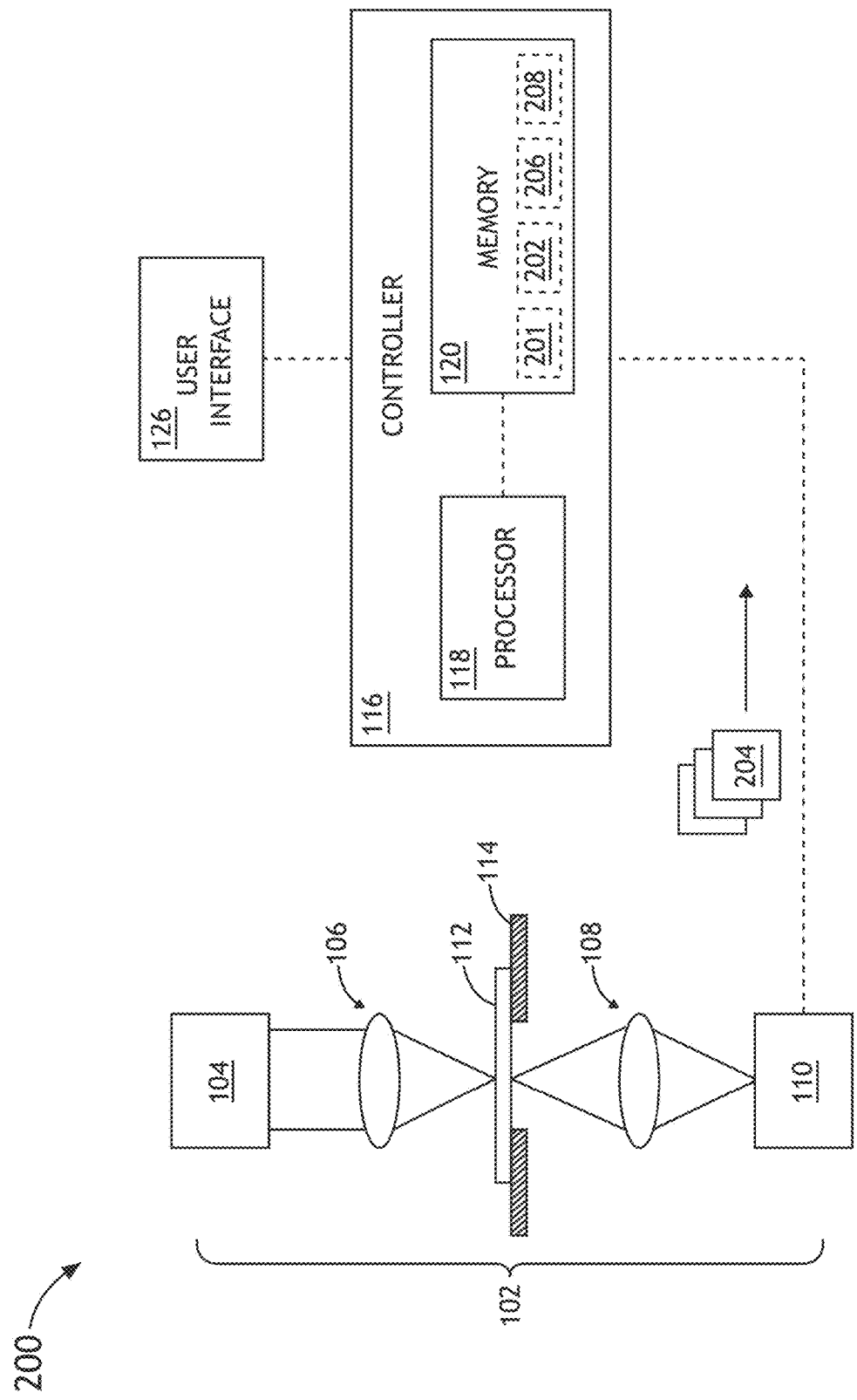
FIG. 2A illustrates a block diagram view of a design-assisted block-to-block reticle inspection system, in accordance with one or more embodiments of the present disclosure.

FIG. 2A illustrates a reticle inspection system 200 for performing design assisted block-to-block reticle inspection, in accordance with one or more embodiments of the present disclosure. It is noted herein that the various system and method embodiments described previously herein should be interpreted to extend to system 200 unless otherwise noted.

Embodiments of system 200 serve to identify block patterns that occur multiple times in a die by analyzing the design database associated with the reticle 112. Additional embodiments may serve to store the output of the design analysis into memory 120 (e.g., stored in GDSII file).

In one embodiment, the one or more processors 118 of the controller 116 may execute a design-assisted block-to-block inspection module 202 maintained in memory 120 in order to carry out a designed assisted (e.g., design database assisted) block-to-block inspection of the reticle 112 using the imagery data 204 acquired from the reticle 112. In another embodiment, a design database 206 may be stored in memory 120 and utilized by the controller 116 when carrying out the process described further herein. It is noted herein that the design data may be stored in any format known in the art including, but not limited to, a GDSII format. In another embodiment, the design-assisted block-to-block inspection module 202 may analyze the design database 206 in order to identify block patterns that occur repeatedly in the die of the reticle 112. After analysis, the module 202 may store the acquired repeating block spatial information (e.g., location, size and pitch) in memory. For example, the information may be stored in a GDSII, whereby each layer in a GDSII file stores rectangles representing a matched block.

In one embodiment, upon acquiring image 204, the detector 110 may transmit the swath image 204 to the controller 116. In one embodiment, the controller 116 may store the acquired image 204 in an image database 201. In another embodiment, the design-based repeating block data acquired the module 202 may be associated with the reticle 112 and stored in a merged database 208 (e.g., file indicating the association between design data and reticle 112). In another embodiment, as described further herein, the data of image 204 may then be compared to the merged database 208 in order to detect one or more defects in repeating blocks of image 204.

The design-assisted block-to-block inspection module 202 may include a set of program instructions configured to cause the one or more processors 118 to execute any of the steps described throughout the present disclosure. In one embodiment, the design-assisted block-to-block inspection module 202 may cause the one or more processors 118 to: identify a set of repeating blocks of a reticle 112 within a design database 206 for the reticle 112; determine one or more spatial characteristics associated with the set of repeating blocks of the reticle 112 (e.g., based on the design data); store the one or more spatial characteristics associated with the set of repeating blocks of the reticle 112 (e.g., store in memory 120); acquire an image 204 of a portion of the reticle 112 with a reticle inspection sub-system 102; identify a first portion of the acquired image corresponding with a first member of the set of repeating blocks according to the stored spatial characteristics associated with the set of repeating blocks; identify a second portion of the acquired image that corresponds to a second member of the set of repeating blocks according to the stored spatial characteristics associated with the set of repeating blocks; align the first portion of the acquired image and the second portion of the acquired image; generate a difference of image by performing a subtraction routine on the first portion of the acquired image and the second portion of the acquired image; and identify one or more defects on the reticle 112 with the generated difference image.

It is recognized herein that the various system and method embodiments described previously herein should be interpreted to extend to the design-assisted block-to-block module 202 unless otherwise noted.

It is noted herein that a semiconductor chip design data may include what is known as a "floorplan," which contains placement information for repeating structures. It is further noted herein that this information may be extracted from the physical design of a chip commonly stored in GDSII file formats. The structural behavior or process-design interactions may be a function of the context (surroundings) of one or more structures. By using the floor plan, the analysis proposed can identify repeating blocks of structures.

Figure 2B:
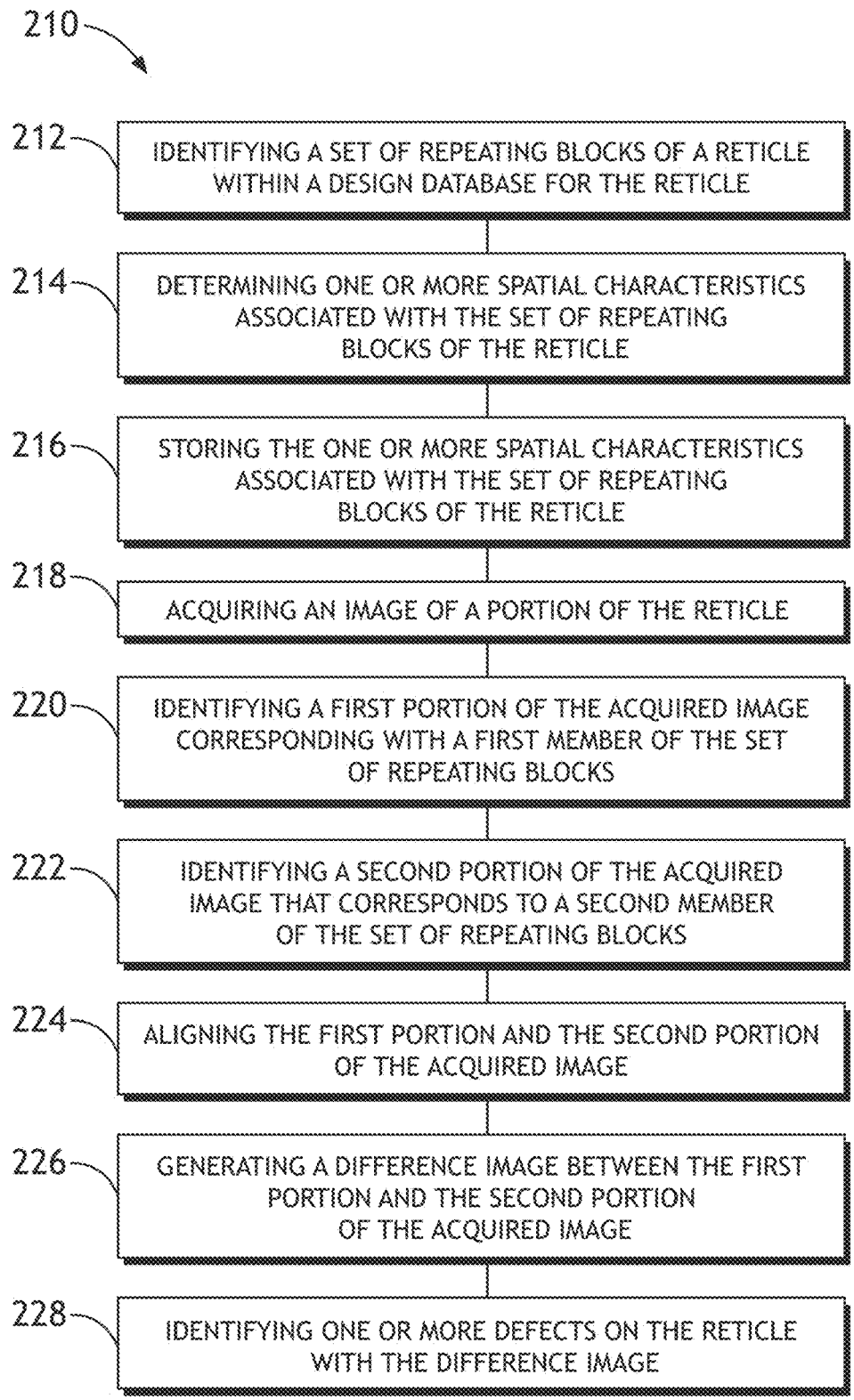
FIG. 2B illustrates a high-level process flow diagram indicating steps associated with an implementation of a design-assisted block-to-block inspection process, in accordance with one or more embodiments of the present invention.

The term "design data" as used in the present disclosure generally refers to the physical design of an integrated circuit and data derived from the physical design through complex simulation or simple geometric and Boolean operations. In addition, an image of a reticle 112 acquired by a reticle inspection system and/or derivatives thereof may be used as a proxy or proxies for the design data. Such a reticle image or a derivative thereof may serve as a substitute for the design layout in any embodiments described herein that uses design data. Design data and design data proxies are described in U.S. Pat. No. 7,676,007 by Kulkarni issued on Mar. 9, 2010; U.S. patent application Ser. No. 13/115,957 by Kulkarni filed on May 25, 2011; U.S. Pat. No. 8,041,103 by Kulkarni issued on Oct. 18, 2011; and U.S. Pat. No. 7,570,796 by Zafar et al. issued on Aug. 4, 2009, all of which are incorporated herein by reference. Further, the use of design data in directing inspection processes is described generally in U.S. patent application Ser. No. 13/339,805 to Park, filed on Feb. 17, 2012, which is incorporated herein by reference in the entirety FIG. 2B illustrates a flow diagram depicting a process 210 for database assisted block-to-block reticle inspection, in accordance with one or more embodiments of the present disclosure.

In step 212, a set of repeating blocks of a reticle 112 is identified within a design database for the reticle 112. For example, the controller 116 of system 200 may identify a set of repeating blocks of a reticle 112 in the stored design data 206 associated with the reticle 112 in question. In one embodiment, the controller 116 may process the post-OPC design database and search for repeating blocks (RB). In one embodiment, this can be performed as part of database preparation in which polygons representing patterns are re-organized and/or fractured. For example, the controller 116 of system 200 may identify a set of repeating blocks of the reticle 112 within the database for the reticle. For instance, the additional process may include, but is not limited to, polygon fracturing, polygon biasing, and database format conversion. In another embodiment, this can also be done as a separate step different from the normal data-preparation operations. In another embodiment, searching for repeating blocks may be carried out by analyzing the hierarchical trees in the design database 206.

In step 214, one or more spatial characteristics associated with the set of repeating blocks of the reticle are determined. For example, the controller 116 of system 200 may identify one or more spatial characteristics, present in the design data base 206, associated with the set of repeating blocks of the reticle 112. For instance, the spatial characteristics identified by the controller 116 may include, but are not limited to, location of one or more blocks (e.g., x-y coordinates), the size of one or more blocks and the pitch associated with two or more repeating blocks.

In step 216, the one or more spatial characteristics associated with the set of repeating blocks of the reticle 112 are stored. For example, the controller 116 of system 200 may store one or more spatial characteristics associated with the set of repeating blocks of the reticle 112 in memory 120. For instance, the spatial characteristics of the repeating blocks may be stored in a GDSII format in memory 120, with each layer in a GDSII file storing rectangles representing a matched block.

In step 218, an image of a portion of the reticle 112 is acquired. For examples, as shown in FIG. 2A, a reticle inspection sub-system 102 may acquire an image 204 from the reticle 112. In another embodiment, the detector 110 of the reticle inspection sub-system 102 may transmit the acquired image 204 to the controller 116. Further, the image 204 may be stored in memory 120 in an image database 201.

In step 220, a first portion of the acquired image corresponding with a first member of the set of repeating blocks is identified according to the stored spatial characteristics associated with the set of repeating blocks. For example, the controller 116 of system 200 may identify a first portion of the acquired image 204 corresponding with a first member of the set of repeating blocks according to the stored spatial characteristics (e.g., stored in memory 105) associated with the set of repeating blocks. In this regard, the controller 116 may match a first portion of the acquired image 204 with a first member of the set of repeating blocks (found via design data analysis above) according to the stored spatial characteristics associated with the set of repeating blocks.

In step 222, a second portion of the acquired image corresponding with a second member of the set of repeating blocks is identified according to the stored spatial characteristics associated with the set of repeating blocks. For example, the controller 116 of system 200 may identify a second portion of the acquired image 204 corresponding with a second member of the set of repeating blocks according to the stored spatial characteristics (e.g., stored in memory 120) associated with the set of repeating blocks. In this regard, the controller 116 may match a second portion of the acquired image 204 with a second member of the set of repeating blocks (found via design data analysis above) according to the stored spatial characteristics associated with the set of repeating blocks.

In step 224, the first portion of the acquired image and the second portion of the acquired image are aligned. For example, the controller 116 of system 200 may align the identified first portion (from step 220) of the acquired image 204 with the identified second portion (from step 222) of the acquired image 204. It is recognized herein that the alignment of the first portion and the second portion may be carried out by any feature recognition and digital imagery process known in the art and/or describe herein.

In step 226, a difference of image is generated by performing a subtraction routine on the first portion of the acquired image and the second portion of the acquired image. For example, following alignment in step 224, the controller 116 of system 200 may generate a difference of image between the first portion of the acquired image 204 and the second portion of the required image. For instance, the controller 116 may calculate a difference image by performing a subtraction routine (e.g., subtraction, weighted subtracted, and the like) on the first portion of the acquired image 204 and the second portion of the acquired image 204. For example, the controller 116 may calculate a difference image by subtracting the intensity values of pixels of the first portion from the intensity values of the pixels of the second portion (or vice-versa).

In step 228, one or more defects on the reticle are identified with the generated difference image. For example, following the difference calculation of step 226, the controller 116 of system 200 may identify one or more defects in the reticle 112. For instance, the controller 116 of system 200 may identify one or more defects in the reticle 112 by identifying a region of the difference image having an intensity value (e.g., absolute intensity) that exceeds a selected threshold. It is noted that in regions without defects the difference image may yield a nominally null result, with the presence of a defect causing an intensity signal to deviate from zero.

In a further step, the controller 116 may associate the stored spatial characteristics associated with the set of repeating blocks with the reticle 112. In another step, the controller 116, following associating the stored spatial characteristics associated with the set of repeating blocks with the reticle 112, may inspect the reticle 112 in an environment where the design database for the reticle 112 is unavailable. In another step, the controller 116 may acquire an image of a portion of the reticle 112 with the reticle inspection sub-system 102. In another step, the controller 116 may identify a first portion of the acquired image corresponding to a first member of the set of repeating blocks according to the stored special characteristics associated with the set of repeating blocks. In another step, the controller 116 may identify a second portion of the acquired image corresponding to a second member of the set of repeating blocks according to the stored special characteristics associated with the set of repeating blocks. In another step, the controller 116 may align the first portion of the acquired image and the second portion of the acquired image. In another step, the controller 116 may generate a difference of image by performing a subtraction routine on the first portion of the acquired image and the second portion of the acquired image. In another step 116, the controller 116 may identify one or more defects on the reticle with the generated difference image.

Figure 2C:
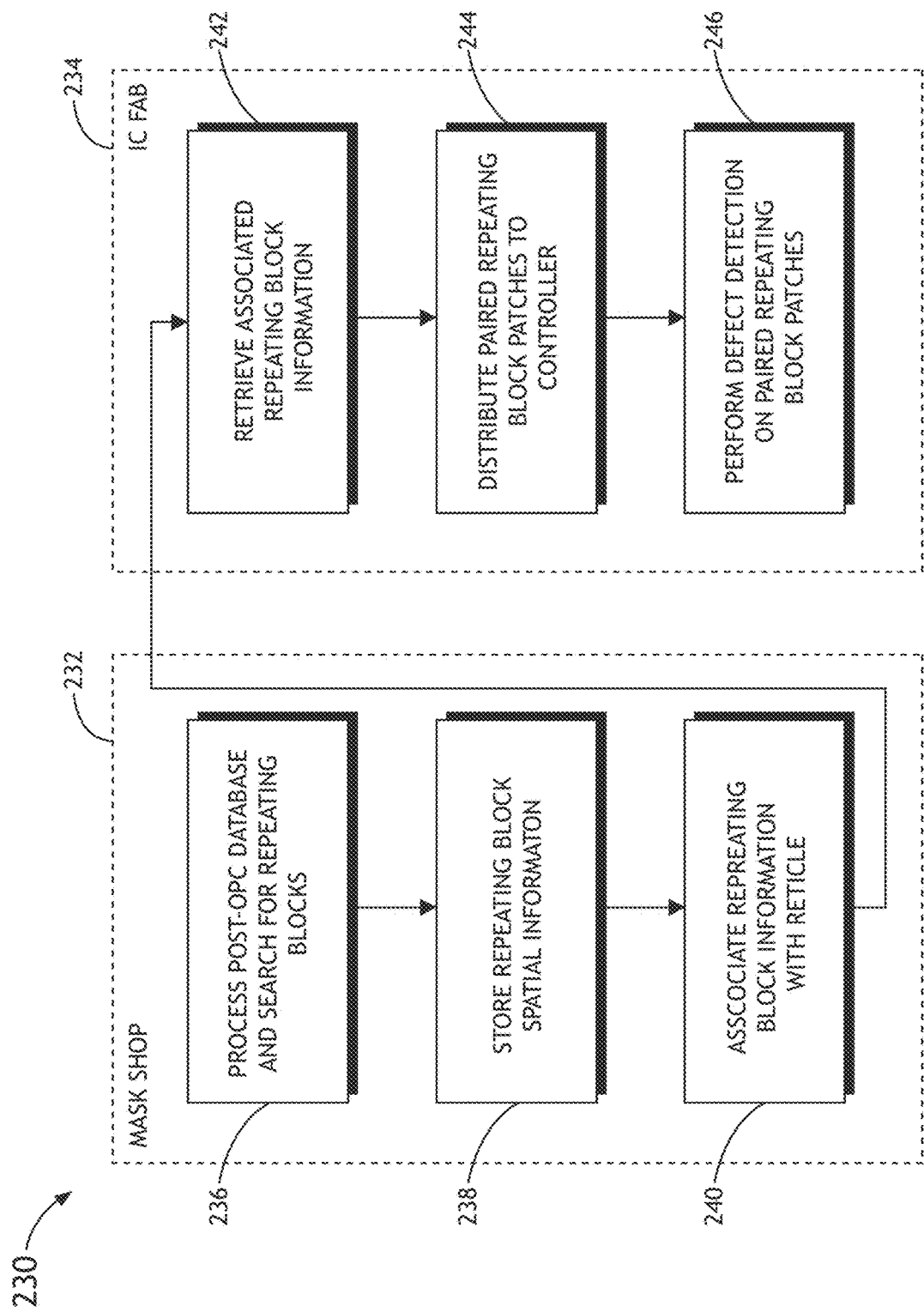
FIG. 2C illustrates a flow diagram depicting a process for design-assisted block-to-block reticle inspection, in accordance with one or more embodiments of the present disclosure.

FIG. 2C illustrates a high-level process flow diagram 230 indicating steps associated with an implementation of a design-assisted block-to-block inspection, in accordance with one or more embodiments of the present invention. It is noted herein that the previous method and system embodiments described previously herein should be interpreted to extend to the process 230 unless otherwise noted. It is noted herein that, in one non-limiting example, steps 236-240 may occur in a mask shop 232, while steps 242-246 take place on the integrated circuit fabrication floor 234.

In step 236, a post-OPC design data base is processed and repeating blocks are searched, as described previously herein. In step 238, the information associated with the repeating blocks is stored, as described previously herein. It is noted herein the repeating block information is saved so that it can be conveyed together with the reticle for subsequent inspections. Once a reticle passes inspection, CD and registration metrology at the mask shop, it starts its productive, high-volume manufacturing life in the wafer (IC) fab. One reticle is used to print a layer of many identical integrated circuits. A reticle 112 can be used for months or years. During this time, the reticle 112 needs to be occasionally inspected. Reticles can be damaged by photo-chemical reactions and electrostatic discharge. The wafer fab has reticle inspection devices for this purpose. Maintaining and retrieving post-OPC databases of all reticles in use at the wafer fab is a burden. The size of a reticle database could be hundreds of gigabytes. Inspecting reticle at the wafer fab without the use of its database is desired. The repeating block information saved at 238 is significantly smaller than the reticle database and it enables block-to-block inspection at the wafer fab.

In step 240, the repeating block spatial information (e.g., size, pitch and location) is associated with, or conveyed to, the reticle 112. In this regard, the repeating block information is transferred from the mask shop 232 to the IC fab 234 together with the actual reticle 112, or mask. Further, the IC fab 234 maintains the repeating block data and its association with a particle reticle, or mask.

By way of non-limiting example, the stored repeating block information may be merged (or associated with) an inspection report associated with the reticle 112. It is recognized herein that this optional step is desirable in cases where a user may want to consolidate all reticle information from a mask shop into a single file. The repeating block information is compact in size relative to a reticle data. For example, one single block may only need 32 bytes (with two vertices) and assuming there are one million repeating blocks in a reticle, the repeating block information may be on the order of 32 MB. This is in comparison to a reticle database, which may be on the order of 100 GB to 1 TB per reticle. As such, it would be advantageous to pass the repeating block information to the IC fab 234 and to use it for block-to-block reticle inspection in the IC fab 234, where the design database is not available.

In step 242, the associated repeating block information is retrieved. For example, a user (or controller) in the IC Fab 234 may retrieve the repeating block information associated with the reticle 112 (from step 240 of Mask Shop 232).

In step 244, paired repeating block patches are distributed to controller 116. For example, a user (or controller 116) in the IC Fab 234 may perform a patch cutting for each swath of an acquired reticle image (e.g., 204). For example, the controller 116 may import the repeating block (e.g., rectangles) and pitches for each matched block within the swath. Further, for each paired repeating blocks (RB), the corresponding patch images may be distributed to the controller 116 (e.g., one or more processors 118).

In step 246, defect detection is performed on the paired repeating block patches. For example, the controller 116 may perform any inspection algorithm known in the art on the paired repeating blocks including, but not limited to, image registration, tool noise reduction/compensation, and defect detection.

It is recognized herein that the embodiments of processes 210 and 230 provide for accurate reference finding that goes beyond a single patch (e.g., typically 1024 pixels in width) in an IC fab without a database. It also eliminates the need to have rule-based algorithms attempting to separate real defects from legitimate pattern differences.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

It is further contemplated that each of the embodiments of the method described above may include any other step(s) of any other method(s) described herein. In addition, each of the embodiments of the method described above may be performed by any of the systems described herein.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. A method for design database assisted block-to-block reticle inspection comprising:

identifying, with one or more processors, a set of repeating blocks of a single-die reticle within a design database of the reticle, wherein the identifying a set of repeating blocks of the single-die reticle within the database for the single die reticle is performed by examining a hierarchy in the database for the single-die reticle;

determining, with the one or more processors, one or more spatial characteristics associated with the set of repeating blocks of the single-die reticle;

storing, in memory, the one or more spatial characteristics associated with the set of repeating blocks of the single-die reticle;

acquiring an image of a portion of a single die of the single-die reticle with a reticle inspection sub-system;

identifying, with the one or more processors, within the single die of the single-die reticle, a first portion of the acquired image corresponding with a first member of the set of repeating blocks according to the stored spatial characteristics associated with the set of repeating blocks by matching the first portion of the acquired image with the first member of the set of repeating blocks found within the design database;

identifying, with the one or more processors, within the single die of the single-die reticle, a second portion of the acquired image that corresponds to a second member of the set of repeating blocks according to the stored spatial characteristics associated with the set of repeating blocks by matching the second portion of the acquired image with the second member of the set of repeating blocks found within the design database;

aligning, with the one or more processors, the first portion of the acquired image and the second portion of the acquired image;

generating, with the one or more processors, a difference image by performing a subtraction routine on the first portion of the acquired image and the second portion of the acquired image; and identifying, with the one or more processors, one or more defects within the single die on the single-die reticle with the generated difference image, wherein resultant repeating block information is merged with an inspection report associated with the single-die reticle.

2. The method of claim 1, wherein the generating a difference of image by performing a subtraction routine on the first portion of the acquired image and the second portion of the acquired image comprises:

determining a difference in intensity values of the first portion of the acquired image and the second portion of the acquired image.

3. The method of claim 1, wherein identifying a set of repeating blocks of the single-die reticle within the database for the single-die reticle comprises:

performing one or more additional processes on the design database for the single-die reticle.

4. The method of claim 3, wherein the one or more additional processes comprise:

at least one of polygon fracturing, polygon biasing, and database format conversion.

5. The method of claim 1, further comprising:

associating the stored spatial characteristics associated with the set of repeating blocks with the single-die reticle;

upon associating the stored spatial characteristics associated with the set of repeating blocks with the single-die reticle, inspecting the single-die reticle in an environment where the design database for the single-die reticle is unavailable;

acquiring an image of a portion of the single-die reticle with the reticle inspection sub-system;

identifying a first portion of the acquired image corresponding to a first member of the set of repeating blocks according to the stored special characteristics associated with the set of repeating blocks;

identifying a second portion of the acquired image corresponding to a second member of the set of repeating blocks according to the stored special characteristics associated with the set of repeating blocks;

aligning the first portion of the acquired image and the second portion of the acquired image;

generating a difference of image by performing a subtraction routine on the first portion of the acquired image and the second portion of the acquired image; and identifying one or more defects on the single-die reticle with the generated difference image.

6. A system comprising:

a reticle inspection sub-system configured for scanning a swath image of a portion of a single-die reticle with a reticle inspection system, wherein the reticle inspection sub-system includes one or more illumination sources, a set of illumination optics and one or more detectors; and a controller including one or more processors configured to execute a set of program instructions maintained on a memory, the program instructions configured to cause the one or more processors to:

identify a set of repeating blocks of a single-die reticle within a design database of the reticle, wherein the identifying a set of repeating blocks of the single-die reticle within the database for the single die reticle is performed by examining a hierarchy in the database for the single-die reticle;

determine one or more spatial characteristics associated with the set of repeating blocks of the single-die reticle;

store the one or more spatial characteristics associated with the set of repeating blocks of the single-die reticle acquire an image of a portion of a single die of the single-die reticle with a reticle inspection sub-system;

identify, within the single die, a first portion of the acquired image corresponding with a first member of the set of repeating blocks according to the stored spatial characteristics associated with the set of repeating blocks by matching the first portion of the acquired image with the first member of the set of repeating blocks found within the design database;

identify, within the single die, a second portion of the acquired image corresponding with a second member of the set of repeating blocks according to the stored spatial characteristics associated with the set of repeating blocks by matching the second portion of the acquired image with the second member of the set of repeating blocks found within the design database;

align the first portion of the acquired image and the second portion of the acquired image;

generate a difference of image by performing a subtraction routine on the first portion of the acquired image and the second portion of the acquired image; and identify one or more defects within the single die on the single-die reticle with the generated difference image, wherein resultant repeating block information is merged with an inspection report associated with the single-die reticle.

7. The system of claim 6, wherein the generating a difference of image by performing a subtraction routine on the first portion of the acquired image and the second portion of the acquired image comprises:

determining a difference in intensity values of the first portion of the acquired image and the second portion of the acquired image.

8. The system of claim 6, wherein identifying a set of repeating blocks of the single-die reticle within the database for the single-die reticle comprises:

performing one or more additional processes on the design databased for the single-die reticle.

9. The system of claim 8, wherein the one or more additional processes comprise:

at least one of polygon fracturing, polygon biasing, and database format conversion.

10. The system of claim 6, wherein the program instructions configured to cause the one or more processors to:
associate the stored spatial characteristics associated with the set of repeating blocks with the single-die reticle;
upon associating the stored spatial characteristics associated with the set of repeating blocks with the single-die reticle, inspecting the reticle in an environment where the design database for the single-die reticle is unavailable;
acquire an image of a portion of the single-die reticle with the reticle inspection sub-system;
identify a first portion of the acquired image corresponding to a first member of the set of repeating blocks according to the stored special characteristics associated with the set of repeating blocks;
identify a second portion of the acquired image corresponding to a second member of the set of repeating blocks according to the stored special characteristics associated with the set of repeating blocks;
align the first portion of the acquired image and the second portion of the acquired image;
generate a difference of image by performing a subtraction routine on the first portion of the acquired image and the second portion of the acquired image; and
identify one or more defects on the single-die reticle with the generated difference image.

11. A system comprising:
a controller including one or more processors configured to execute a set of program instructions maintained on a memory, the program instructions configured to cause the one or more processors to:
identify a set of repeating blocks of a single-die reticle within a design database of the single-die reticle, wherein the identifying a set of repeating blocks of the single-die reticle within the database for the single die reticle is performed by examining a hierarchy in the database for the single-die reticle;
determine one or more spatial characteristics associated with the set of repeating blocks of the single-die reticle;
store the one or more spatial characteristics associated with the set of repeating blocks of the single-die reticle
receive an image of a portion of the single-die reticle from a reticle inspection sub-system;
identify, within a single die of the single-die reticle, a first portion of the acquired image corresponding with a first member of the set of repeating blocks according to the stored spatial characteristics associated with the set of repeating blocks by matching the first portion of the acquired image with the first member of the set of repeating blocks found within the design database;
identify, within the single die, a second portion of the acquired image corresponding with a second member of the set of repeating blocks according to the stored spatial characteristics associated with the set of repeating blocks by matching the second portion of the acquired image with the second member of the set of repeating blocks found within the design database;
align the first portion of the acquired image and the second portion of the acquired image;
generate a difference of image by performing a subtraction routine on the first portion of the acquired image and the second portion of the acquired image; and
identify one or more defects within the die on the single-die reticle with the generated difference image, wherein resultant repeating block information is merged with an inspection report associated with the single-die reticle.

12. The system of claim 11, wherein the generating a difference of image by performing a subtraction routine on the first portion of the acquired image and the second portion of the acquired image comprises:
determining a difference in intensity values of the first portion of the acquired image and the second portion of the acquired image.

13. The system of claim 11, wherein identifying a set of repeating blocks of the single-die reticle within the database for the single-die reticle comprises:
performing one or more additional processes on the design database for the single-die reticle.

14. The system of claim 13, wherein the one or more additional processes comprise:
at least one of polygon fracturing, polygon biasing, and database format conversion.

15. The system of claim 11, wherein the program instructions configured to cause the one or more processors to:
associate the stored spatial characteristics associated with the set of repeating blocks with the single-die reticle;
upon associating the stored spatial characteristics associated with the set of repeating blocks with the reticle, inspecting the single-die reticle in an environment where the design database for the single-die reticle is unavailable;
acquire an image of a portion of the single-die reticle with the single-die reticle inspection sub-system;
identify a first portion of the acquired image corresponding to a first member of the set of repeating blocks according to the stored special characteristics associated with the set of repeating blocks;
identify a second portion of the acquired image corresponding to a second member of the set of repeating blocks according to the stored special characteristics associated with the set of repeating blocks;
align the first portion of the acquired image and the second portion of the acquired image;
generate a difference of image by performing a subtraction routine on the first portion of the acquired image and the second portion of the acquired image; and
identify one or more defects on the single-die reticle with the generated difference image.

* * * * *